United States Patent [19]

Conrad et al.

[11] 4,130,509
[45] Dec. 19, 1978

[54] PERFUME COMPOSITIONS CONTAINING CIS- AND TRANS-TRIMETHYLCYCLOHEXYLETHYL ETHERS

[75] Inventors: Jens Conrad, Hilden; Klaus Bruns, Krefeld-Traar; Peter Meins, Mettmann, all of Germany

[73] Assignee: Henkel Kommanditgesellschaft auf Aktien (Henkel KGaA), Düsseldorf-Holthausen, Germany

[21] Appl. No.: 862,675

[22] Filed: Dec. 21, 1977

[30] Foreign Application Priority Data

Dec. 23, 1976 [DE] Fed. Rep. of Germany ....... 2658567

[51] Int. Cl.$^2$ ............................................. C11B 9/00
[52] U.S. Cl. ..................... 252/522; 252/89 R; 252/108; 252/305; 424/14; 428/358; 252/8.6; 568/579
[58] Field of Search ...................... 260/611 R; 252/522

[56] References Cited

U.S. PATENT DOCUMENTS

| 2,821,547 | 1/1958 | Klein ................................. 260/611 R |
| 3,845,141 | 10/1974 | Naegli ................................. 252/522 |
| 3,876,561 | 4/1975 | Naegli ................................. 252/522 |
| 3,953,471 | 4/1976 | Corbier ............................ 260/611 R |

*Primary Examiner*—Veronica O'Keefe
*Attorney, Agent, or Firm*—Hammond & Littell

[57] ABSTRACT

A perfumery composition consisting essentially of from 1% to 50% by weight of cis- and trans-trimethylcyclohexylethyl ethers of the formulae:

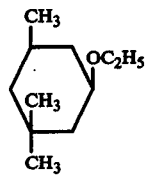

and 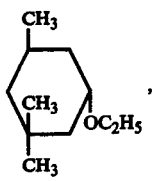

and the remainder customary constituents of perfumery compositions; and a process for producing trans-3,3,5-trimethylcyclohexylethyl ether by means of hydrogenation of 3,3,5-trimethylcyclohexenylethyl ether with dry nickel catalysts at a temperature of 150°–200° C and at 10–200 bar hydrogen pressure and processing of the hydrogenation product in the conventional manner.

4 Claims, No Drawings

PERFUME COMPOSITIONS CONTAINING CIS- AND TRANS-TRIMETHYLCYCLOHEXYLETHYL ETHERS

OBJECTS OF THE INVENTION

An object of the present invention is the development of a perfumery composition containing ether compounds having natural and pleasing fragrances, which are combinable with other perfumes in widely varying ratios.

Another object of the present invention is the production of cis- and trans-trimethylcyclohexylethyl ethers of the formulae

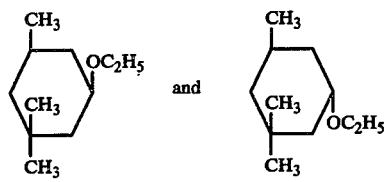

as perfumes.

A yet further object of the present invention is the production of a perfumery composition consisting essentially of from 1% to 50% by weight of the above cis- and trans-trimethylcyclohexylethyl ethers and the remainder customary perfume constituents.

A still further object of the present invention is an improvement in the process of supplying a pleasing odor to a product by incorporating a perfume therein, by utilizing from 0.05 to 2% by weight of the above cis- and trans-trimethylcyclohexylethyl ethers as said perfume.

A yet further object of the present invention is the development of an improved process for producing trans-3, 3,5-trimethylcyclohexylethyl ether by means of hydrogenation of 3,3,5-trimethylcyclohexenylethyl ether with dry nickel catalysts at a temperature of 150°-200° C. and at 10-200 bar hydrogen pressure and thereafter processing the hydrogenation product in known manner.

These and other objects of the invention will become more apparent as the description thereof proceeds.

DESCRIPTION OF THE INVENTION

It has been found that cis- and trans-trimethylcyclohexylethyl ethers are valuable new perfumes having distinctive fragrances which have not previously been described.

More particularly the present invention relates to a perfumery composition consisting essentially of from 1% to 50% by weight of cis- and trans-trimethylcyclohexylethyl ethers of the formula

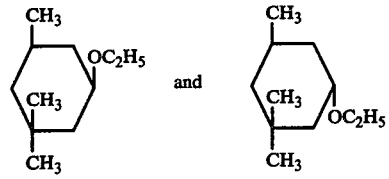

and the remainder customary constituents of perfumery compositions.

The invention also relates to an improved process for producing trans-3,3,5-trimethylcyclohexylethyl ether, with only small admixtures of cis-ether, comprising hydrogenating 3,3,5-trimethylcyclohexenylethyl ether with dry nickel hydrogenation catalysts at an elevated temperature and thereafter processing the hydrogenation product in known manner.

More particularly, the present invention provides an improved process for making trans-3,3,5trimethylcyclohexylethyl ether which comprises hydrogenating 3,3,5-trimethylcyclohexenylethyl ether in the presence of a dry nickel catalyst, preferably Girdler-nickel 49A, at a temperature of 150°-200° C. and at 10 to 200 bar hydrogen pressure, and subsequently processing the hydrogenation product in known manner.

The cis- and trans- trimethylcyclohexylethyl ethers which are used as perfumes in accordance with the present invention can be produced by conventional methods, as e.g. those of C. A. Grob, W. Schwarz and H. P. Fischer as described in Helv. Chem. Acta 47, 1398, 1399 (1964). Thus, isophorone can first be converted into cyclohexanols and during this hydrogenation of isophonone a preponderant quantity of cis-3,3,5 trimethylcyclohexanol is produced together with a minor amount of trans-3,3,5 trimethylcyclohexanol, with a ratio of cis: trans of approximately 80 : 20.

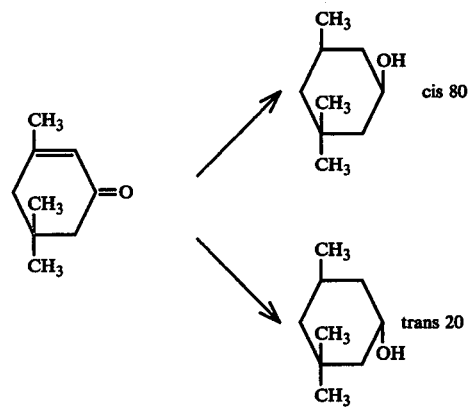

By means of metallization with sodium hydride and conversion with an ethyl halide the corresponding cis-ether can be produced with good yields from the cis-alcohol although the rate of reaction is slow.

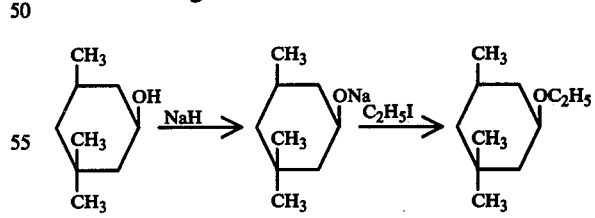

cis-3,3,5 trimethylcyclo-
hexylethyl ether (93% of
the theoretical yield)

In the corresponding conversion of the trans-alcohol considerably more severe conditions are required, as for example, boiling for several days with silver oxide and ethyl iodide, and despite such severe conditions poor yields are nevertheless obtained.

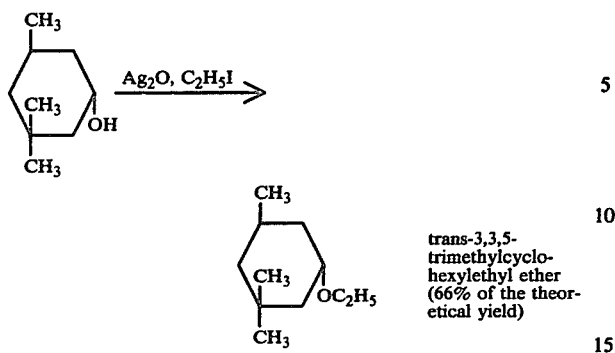

Both the cis- and the trans-3,3,5 trimethylcyclohexylethyl ethers have characteristic frangrances which make them suitable as novel perfumes. A particular advantage of the perfumes of the present invention is their very good ability to be combined into new kinds of fragrances.

The fragrances of both products of the invention can be described as follows:

cis-3,3,5 trimethylcyclohexylethyl ether: fruity, minty, herbal; weaker in smell than the trans-ether; fruity fragrance strongly emphasized.

trans-3,3,5-trimethylcyclohexylethyl ether: herbal, minty, fresh; essentially more intense in smell than the cis-ether; herbal fragrance strongly emphasized.

The trans-ether constitutes far and away the more valuable substance in perfuming applications.

As already mentioned above, conventional methods of producing the two ethers of the present invention, particularly those for the production of the trans-ether, are technically unsatisfactory processes. They require long reaction times and, furthermore give only moderate yields in the case of the trans-ether. The discovery of a technically feasible process for the production of the trans-3,3,5 trimethylcyclohexylethyl ether is therefore a highly desireable goal.

An improved process for producing trans-3,3,5 trimethylcyclohexylethyl ether has now been found in which an enol ether, which is easily produced in known manner from dihydroisophorone, is hydrogenated by means of dry nickel catalysts, particularly Girdler-nickel 49 A, at a temperature of 150° to 200° C. and at 10 to 200 bar hydrogen pressure, and the hydrogenation product is treated in the usual way. This improved method produces a very high proportion of the transether, as for example over 90% by weight, and only a minor amount of the cis-ether, as for example under 10% by weight. In a typical operation demonstrating the high selectivity of the process, trans-3,3,5 trimethylcyclohexylethyl ether is produced in an amount of approximately 95% by weight of the hydrogenation product, along with very small amounts of cis-3,3,5-trimethylcyclohexylethyl ether as approximately 5% by weight of the hydrogenation product. The reaction proceeds according to the following scheme:

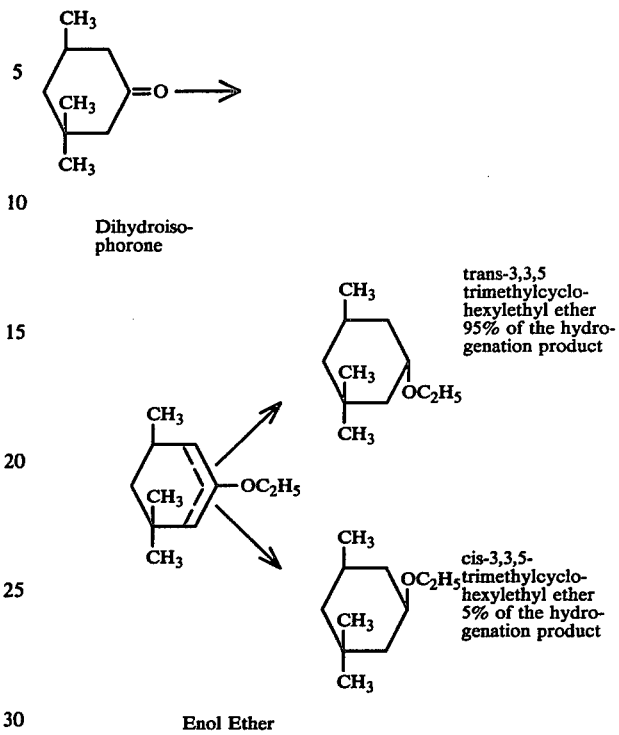

The stereochemical configuration of the components of the hydrogenation products was determined by gas-chromatographic comparison with conventionally produced substances of known stereochemistry.

Although the hydrogenation of enol ether can be advantageously accomplished without solvents, a dilution with an alcohol like ethanol is, however, also possible. In so doing it is essential to exclude water since otherwise the enol ether would be partially split, leading to the formation of trimethylcyclohexanone and trimethylcyclohexanol as by-products, which can be removed only with difficulty and which adulterate the odor of the end product. This accounts for the use in the process of the present invention of non-pyrophoric nickel catalysts, particularly Girdlernickel 49 A, which can be handled in the dry state.

The hydrogenation of enol ethers which, depending on the catalyst used, leads to the saturated ether as well as a more or less strong splitting of the C-O bond, is basically known in the literature.

Investigations have also already been made on the stereochemical course of the hydrogenation of 4-methylcyclohexenylethyl ether by means of precious metal catalysts (see S. Nishimura, M. Katagiri, T. Watanabe, M. Uramoto, Bull Chem. Soc . Japan, 44, 166–172 (1971)).

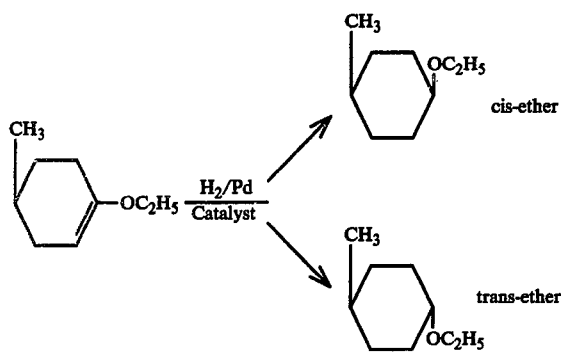

Through this process mixtures of cis- and trans- ether are generally produced, with the cis-derivative always preponderant. It is, in fact, feasible under quite special mild conditions to very selectively produce the cis-ether, as for example, through hydrogenation by means of palladium in ethanol at 25° C. under normal pressure but it is, however, not possible to so influence the process that the trans-ether is preferentially formed.

It was thus extraordinarily surprising that, during the hydrogenation of an enol ether in accordance with the method according to the present invention, trans-3,3,5 trimethylcyclohexylethyl ether was produced with a very high selectivity along with only very small amounts of cis-3,3,5 trimethylcyclohexylethyl ether.

The cis- and trans-3,3,5 trimethylcyclohexylethyl ethers which are used in accordance with the present invention as perfumes can be mixed with one or more other perfumes in the most varied ratios of quantities to form novel perfume compositions. However, in general, the proportion of cis- and trans-3,3,5 trimethylcyclohexylethyl ethers in the perfume compositions lies in the range of from 1 to 50% by weight, relative to the total composition. The perfume compositions of the invention advantageously contain a content of the above cis- and trans-3,3,5 trimethylcyclohexylethyl ethers, wherein the trans-ether constitutes a major amount, as for example over 90 weight percent, of said content and the cis-ether a minor amount, as for example under 10 weight percent, of said content. In a typical formulation the transand cis-ether content is made up of approximately 95 weight percent trans-3,3,5 trimethylcyclohexylethyl ether and approximately 5 weight percent cis-3,3,5-trimethylcyclohexylethyl ether. The remainder of the composition is conventional perfume constituents. One or more additional perfumes can be used in combination with the ethers of the invention. The perfume compositions of the invention can act directly as perfumes or, as is preferred however, can be used to perfume cosmetics such as creams, lotions, toilet waters, aerosols, toilet soaps, etc. Alternatively, however, they can also be used to improve the odor of industrial products such as washing and cleaning agents, disinfectants, agents for treating textiles, etc.

The invention thus also includes a process of imparting a pleasing odor to a product comprising adding thereto from 0.05% to 2% by weight, relative to the total product, of a perfumery composition containing the ether of the invention as a scenting agent.

The present invention will now be further described by means of the following Examples which are not to be limitative in any manner.

EXAMPLES

EXAMPLE 1

Production of trans-3,3,5 trimethylcyclohexylethyl ether 280 gm (2 moles) of 3,3,5 trimethylcyclohexanone and 355 gm (2 moles) of triethyl orthoformate were added to 2 gm of p-toluenesulfonic acid and stirred for 30 minutes. Subsequently, at normal pressure approximately 200 gm of ethyl formate and ethanol were distilled off (bottom 70° to 115° C., top 56° to 77° C.) and the residue was fractionated in vacuo. 340 gm of enol ether (b.p.$_{17mm}$ 59° to 63° C.) were obtained in quantitative yield.

340 gm of the enol ether obtained as described above were added to 25 gm of Girdler nickel 49 A and heated slowly up to 200° C. in an autoclave at 50 bar hydrogen pressure. At approximately 170° C. hydrogen adsorption commenced. Such absorption terminated within 15 minutes. The mixture was allowed to react further for one hour at 200° C. and at an increased hydrogen pressure of 180 bar. It was then cooled down, and the product was decanted from the catalyst and then fractionated in vacuo. 250 gm, i.e. 74% of the theoretical yield, of 3,3,5 trimethylcyclohexylethyl ether were obtained with a boiling point $_{100mm}$ of 112° to 116° C. and a refractive index $n_\eta^{20}$ = 1.4364. The reaction product consisted of 95% trans-3,3,5 trimethylcyclohexylethyl ether and of only 5% cis-3,3,5 trimethylcyclohexylethyl ether.

EXAMPLE 2

Production of cis-3,3,5 trimethylcyclohexylethyl ether

The preparation was carried out according to the procedure in Helvetica Chimica Acta 47, 1398 (1964). 142 gm of the cis-3,3,5 trimethylcyclohexanol obtained were boiled at reflux with 150 ml toluene and 60 gm sodium hydride for 24 hours.

390 gm of ethyl iodide were slowly dropped into the suspension obtained and the entire mixture was heated again for 36 hours up to 100° C. After the careful addition of 1000 ml of water, the toluene layer was separated off, washed with water until neutral, dried with sodium sulfate and then fractionally distilled. 150 gm of cis-trimethylcyclohexylethyl ether were obtained, corresponding to 90% of the theoretical value, with a boiling point $_{56mm}$ of 108° C. and a refractive index $n_D^{20}$ = 1.4389.

The compounds given in the above Examples have distinctive, pleasing fragrances which render them suitable for producing a wide variety of perfume compositions. Such compositions can be used to perfume a wide variety of products, such as cosmetics, washing agents, soaps as well as technical products in concentrations of approximately 0.05% to 2% by weight. Examples of perfumery compositions having a content of the new perfume ethers in accordance with the invention are given hereinafter.

EXAMPLE 3

| Artificial lavender perfume composition | | | |
|---|---|---|---|
| Trans-3,3,5 trimethylclcyclohexylethyl ether (95% trans-form; 5% cis-form) | 100 | pts. by | wt. |
| Lavendine oil Abrialis | 400 | " " | " |
| Lavender oil acetylated | 375 | " " | " |
| Geranyl acetate | 30 | " " | " |
| Lavender absolute | 25 | " " | " |

-continued

| Artificial lavender perfume composition | | | | |
|---|---|---|---|---|
| Allyl ionone | 20 | " | " | " |
| Citronellol | 20 | " | " | " |
| Ethylamyl ketone | 15 | " | " | " |
| Sandal (H&R) | 10 | " | " | " |
| Cumarin | 5 | " | " | " |
| | 1.000 | " | " | " |

EXAMPLE 4

| Fruity-fresh flower bouquet perfume Compositon | | | | |
|---|---|---|---|---|
| Cis-3,3,5 trimethylcyclohexylethyl ether | 150 | pts. | by | wt. |
| Hydroxycitronellal | 170 | " | " | " |
| Geraniol | 150 | " | " | " |
| Phenylethyl alcohol | 100 | " | " | " |
| Phenylethyldimethyl carbinol | 100 | " | " | " |
| alpha-amylcinnamaldehyde | 100 | " | " | " |
| Terpineol | 60 | " | " | " |
| Linalool | 50 | " | " | " |
| Terpinyl acetate | 25 | " | " | " |
| alpha-ionone | 20 | " | " | " |
| Cumarin | 20 | " | " | " |
| Hydrocinnamyl alcohol | 15 | " | " | " |
| Ethylene brassylate | 10 | " | " | " |
| | 1.000 | " | " | " |

EXAMPLE 5

| Soap perfume composition | | | | |
|---|---|---|---|---|
| Citrenes | 450 | pts. | by | wt. |
| Trans-3,3,5 trimethylcyclohexylethyl ether | 325 | " | " | " |
| Methyl anthralinate | 100 | " | " | " |
| Indole | 5 | " | " | " |
| Bergamot oil | 70 | " | " | " |
| Tolu balsam | 50 | " | " | " |

This soap perfume composition is added to a toilet soap in amounts of from 0.5 to 1% by weight.

The preceeding specific embodiments are illustrative of the practice of the invention. It is to be understood, however, that other expedients known to those skilled in the art or disclosed herein may be employed without departing from the spirit of the invention or the scope of the appended claims.

We claim:

1. A perfumery composition comprising from about 1% to 50% by weight of a perfume selected from the group consisting of
   (1) cis-3,3,5-trimethylcyclohexylethyl ether of the formula

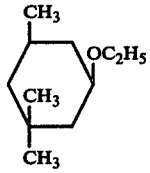

, (2) trans-3,3,5-trimethylcyclohexylethyl ether of the formula

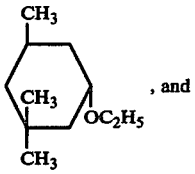

, and (3) mixtures thereof, and the remainder customary constituents of perfumery compositions.

2. The perfumery composition of claim 1 wherein the perfume is a mixture of a major amount of trans-3,3,5-trimethylcyclohexylethyl ether and of a minor amount of cis-3,3,5-trimethylcyclohexylethyl ether.

3. The perfumery composition of claim 2 wherein the weight ratio of trans-ether to cis-ether is approximately 95%: approximately 5%.

4. The perfumery composition of claim 1 which contains one or more additional perfumes.

* * * * *

UNITED STATES PATENT AND TRADEMARK OFFICE
CERTIFICATE OF CORRECTION

PATENT NO. : 4,130,509
DATED : December 19, 1978
INVENTOR(S) : JENS CONRAD et al.

It is certified that error appears in the above-identified patent and that said Letters Patent are hereby corrected as shown below:

Column 7, lines 18-19, in the tabular presentation of components of EXAMPLE 4, the table should include:

Linalyl acetate    30    "    "    "

Signed and Sealed this

Fourth Day of December 1979

[SEAL]

*Attest:*

SIDNEY A. DIAMOND

*Attesting Officer*    *Commissioner of Patents and Trademarks*